US010251584B2

(12) United States Patent
Jin et al.

(10) Patent No.: US 10,251,584 B2
(45) Date of Patent: Apr. 9, 2019

(54) METHOD AND APPARATUS FOR CORRECTION OF NON-INVASIVE BLOOD GLUCOSE MEASUREMENT

(71) Applicant: iiSM Inc., Sejong (KR)

(72) Inventors: Seung Min Jin, Sejong (KR); Il Seung Yang, Sejong (KR); Yun Mi Bae, Sejong (KR); Seong Oak Park, Daejeon (KR); Yu Sic Kim, Daejeon (KR); Du Cheon Choi, Sejong (KR); Mu Hyeop Han, Daejeon (KR)

( * ) Notice: Subject to any disclaimer, the term of this patent is extended or adjusted under 35 U.S.C. 154(b) by 4 days.

(21) Appl. No.: 15/531,646

(22) PCT Filed: Nov. 25, 2016

(86) PCT No.: PCT/KR2016/013685
§ 371 (c)(1),
(2) Date: May 30, 2017

(87) PCT Pub. No.: WO2017/099395
PCT Pub. Date: Jun. 15, 2017

(65) Prior Publication Data
US 2018/0206767 A1  Jul. 26, 2018

(30) Foreign Application Priority Data

Dec. 9, 2015  (KR) .................. 10-2015-0175288

(51) Int. Cl.
*A61B 5/145* (2006.01)
*A61B 5/1455* (2006.01)
(Continued)

(52) U.S. Cl.
CPC ........ *A61B 5/14532* (2013.01); *A61B 5/0033* (2013.01); *A61B 5/0064* (2013.01);
(Continued)

(58) Field of Classification Search
CPC .............. A61B 5/14532; A61B 5/0075; A61B 5/02416; A61B 5/1455; A61B 5/489;
(Continued)

(56) References Cited

U.S. PATENT DOCUMENTS 5,313,941 A * 5/1994 Braig ................. A61B 5/14532
356/41
5,553,613 A * 9/1996 Parker ................ A61B 5/14532
600/316
(Continued)

FOREIGN PATENT DOCUMENTS

CN   1200657 A   3/2001
CN   1616919 A   5/2005
(Continued)

OTHER PUBLICATIONS

Office Action, Chinese Application No. 20168000038241, 5 pgs; 7 pgs translation, dated Dec. 1, 2017.
(Continued)

*Primary Examiner* — Jingge Wu
(74) *Attorney, Agent, or Firm* — Stinson Leonard Street LLP

(57) ABSTRACT

Correction of a non-invasive blood glucose measurement measured from a video image. Correction includes irradiating white light on the skin, filtering the white light reflected from the skin by a first wavelength filter and a second wavelength filter, obtaining a first signal including a blood glucose signal and a pulse signal based on a video image generated by the white light filtered by the first wavelength filter, obtaining a second signal including a pulse signal based on a video image generated by the white light filtered by the second wavelength filter, obtaining a blood glucose signal by subtracting the second signal from the first signal, and calculating the amount of blood glucose in a subcutaneous blood vessel based on the obtained blood glucose
(Continued)

signal. Moreover, fundamental blood glucose signals can be extracted in real time without collecting blood.

12 Claims, 9 Drawing Sheets

(51) Int. Cl.
  *A61B 5/00* (2006.01)
  *A61B 5/024* (2006.01)
  *A61B 5/02* (2006.01)
  *A61B 5/026* (2006.01)
(52) U.S. Cl.
  CPC ........ *A61B 5/0075* (2013.01); *A61B 5/02416* (2013.01); *A61B 5/1455* (2013.01); *A61B 5/7203* (2013.01); *A61B 5/02007* (2013.01); *A61B 5/0261* (2013.01); *A61B 5/489* (2013.01); *A61B 5/7225* (2013.01)
(58) Field of Classification Search
  CPC ... A61B 5/7203; A61B 5/0033; A61B 5/0064; G01J 3/06; G01J 3/12; G01N 21/31
  See application file for complete search history.

(56) References Cited

U.S. PATENT DOCUMENTS

| | | | | |
|---|---|---|---|---|
| 5,666,956 | A * | 9/1997 | Buchert | A61B 5/14532 600/316 |
| 5,983,120 | A * | 11/1999 | Groner | A61B 5/0261 356/364 |
| 6,026,314 | A * | 2/2000 | Amerov | A61B 5/14532 600/316 |
| 6,097,975 | A * | 8/2000 | Petrovsky | A61B 5/1455 600/316 |
| 6,477,393 | B1 | 11/2002 | Chou | |
| 6,804,002 | B2 * | 10/2004 | Fine | A61B 5/14558 356/364 |
| 7,225,005 | B2 * | 5/2007 | Kaufman | A61B 5/14535 600/310 |
| 7,720,527 | B2 | 5/2010 | Kondoh et al. | |
| 9,044,167 | B2 | 6/2015 | Imamura | |
| 2002/0123677 | A1 * | 9/2002 | Miki | A61B 5/14532 600/316 |
| 2002/0190211 | A1 * | 12/2002 | Watanabe | G01J 3/06 250/339.07 |
| 2007/0027374 | A1 * | 2/2007 | Wihlborg | A61B 5/14532 600/322 |
| 2009/0116006 | A1 * | 5/2009 | Tokita | A61B 5/14532 356/300 |
| 2012/0271121 | A1 * | 10/2012 | Della Torre | A61B 5/024 600/301 |
| 2013/0261413 | A1 | 10/2013 | Kawahara et al. | |
| 2015/0216457 | A1 | 8/2015 | Kasahara et al. | |

FOREIGN PATENT DOCUMENTS

| | | |
|---|---|---|
| CN | 102198004 A | 9/2011 |
| CN | 103260515 A | 8/2013 |
| CN | 104000599 A | 5/2014 |
| JP | 09-182739 | 7/1997 |
| JP | 2007-175242 | 7/2007 |
| JP | 2015-142665 A | 8/2015 |
| KR | 10-20100022614 A | 3/2010 |
| KR | 20100022614 A | 3/2010 |
| KR | 10-20100112544 A | 10/2010 |
| KR | 10-20140127505 | 11/2014 |
| WO | WO97/15229 A1 | 5/1997 |

OTHER PUBLICATIONS

Corrected English Translation of Final Rejection dated Jun. 4, 2018 relating to Japanese Application No. 2017-529840, 7 pages.
Office Action, Japanese Patent Application No. 2017-529840, 8 pgs; 9 pgs. translation, dated Dec. 21, 2017.
English Translation of Final Rejection dated Dec. 21, 2017 relating to Japanese Application No. 2017-529840, 7 pages.
Written Opinion, PCT/KR2016/013685, dated Feb. 28, 2017, 5 pgs.
International Search Report, PCT/KR2016/013685, dated Feb. 28, 2017, 3 pgs.

* cited by examiner the pixel where the blood vessel is located the pixel where there is no blood vessel

US 10,251,584 B2

METHOD AND APPARATUS FOR CORRECTION OF NON-INVASIVE BLOOD GLUCOSE MEASUREMENT

CROSS-REFERENCE TO RELATED APPLICATIONS

This application is a national stage application of PCT/KR2016/013685, filed Nov. 25, 2016, which claims priority to Korean application 10-2015-0175288, filed Dec. 9, 2015, the entire contents of which are incorporated herein by reference for all purposes.

TECHNICAL FIELD

The present invention relates to a method and apparatus for correction of blood glucose measurement of a subcutaneous blood vessel, and more specifically, to a method and apparatus for correction of signals other than blood glucose signals by subtracting signals based on white light reflected from the skin.

BACKGROUND

Generally, blood glucose refers to glucose contained in blood. It is essential for a human body to maintain a certain amount of blood glucose to maintain life, and blood glucose that is excessively high induces diabetes. By measuring the amount of blood glucose in blood, it can be figured out whether a certain amount of blood glucose is being maintained. In case blood glucose in an amount outside normal ranges is measured, health can be maintained through appropriate measures.

Methods of blood glucose measurement in a living body are generally classified into invasive methods and non-invasive methods. Invasive methods refer to methods of measuring the concentration of blood glucose in blood by a chemical treatment of a blood sample that was collected by pricking a part of the body, for example, a finger. However, such invasive method presents problems that they may give psychological burden to patients because their fingers have to be pricked to collect blood every time their blood glucose is measured, and an unexpected infection may be induced during the process of collecting blood.

Recently, in response to said problems, there is a growing need for a non-invasive measurement apparatus for measuring blood glucose in a subcutaneous blood vessel without collecting blood. However, a method and apparatus for non-invasive blood glucose measurement using an image sensor have not been introduced so far.

SUMMARY

A method and apparatus for correction of non-invasive blood glucose measurement according to the present invention can use a method of realizing a plurality of pixels from an image obtained by using an image sensor in, and analyzing the image in pixel units, and extracting a signal to be measured in a pixel in a part to be measured. However, a method for non-invasive blood glucose measurement using an image sensor has a disadvantage that due to noise detected together with a blood glucose signal in the reflected light, exact amount of blood glucose cannot be calculated. In addition, when measuring blood glucose signals in real time, signals that are detected in places other than blood vessels may influence the exact measurement value of blood glucose. In particular, blood glucose signals are micro signals that are very precise. Thus, changes in the blood flow rate according to heart beats and skin environment signals according to skin environments of individuals may become noise that interferes with quantitative analysis. Therefore, there is a disadvantage that it is difficult to extract fundamental blood glucose signals of blood glucose that is measured in real time.

Accordingly, the present invention aims to provide a method and apparatus which, in measuring the amount of blood glucose in a subcutaneous blood vessel, measures and analyzes the exact amount of blood glucose by correcting a pulse signal without collecting blood, by using a correction method according to the difference between a first signal that includes a blood glucose signal and a pulse signal and a second signal that includes a pulse signal.

Further, the present invention includes a method and apparatus which correct skin environment signals including signals for at least one of the changes in the blood flow rate, the thickness of the blood vessels, and the skin color, and accordingly can measure the amount of blood glucose more exactly.

DETAILED DESCRIPTION

Figure 1:
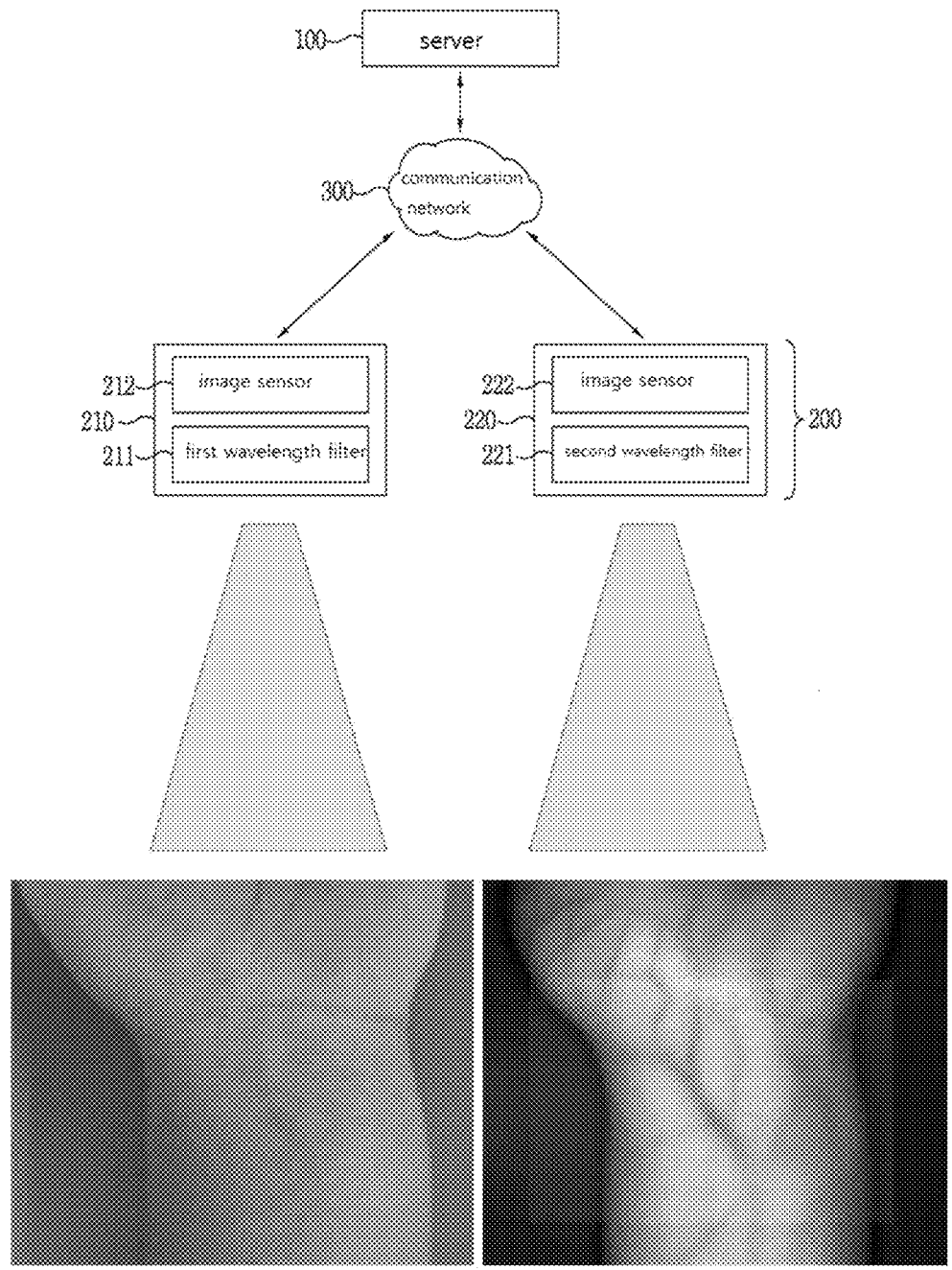
FIG. 1 is a simplified diagram of a system for correction of non-invasive blood glucose measurement according to one embodiment of the present invention.

The present invention provides a method for correction of non-invasive blood glucose measurement. The present method comprises the steps of irradiating white light on the skin by using a white light source, filtering the white light reflected from the skin by a first wavelength filter and a second wavelength filter, obtaining a first signal including a blood glucose signal and a pulse signal based on a video image generated by the white light filtered by the first wavelength filter, obtaining a second signal including a pulse signal based on a video image generated by the white light filtered by the second wavelength filter, obtaining a blood glucose signal by subtracting the second signal from the first signal, and calculating the amount of blood glucose in a subcutaneous blood vessel based on the obtained blood glucose signal.

In one embodiment, a video image generated by the reflected white light filtered by a first wavelength filter includes a third signal which includes a blood glucose signal, a pulse signal, and a skin environment signal from the first region of the skin, and a fourth signal that includes a skin environment signal from the second region of the skin, and the step of obtaining the first signal may obtain the first signal by subtracting the fourth signal from the third signal.

In one embodiment, a video image generated by the reflected white light filtered by a second wavelength filter includes a fifth signal which includes a pulse signal and a skin environment signal from the first region of the skin, and a sixth signal that includes a skin environment signal from the second region of the skin, and the step of obtaining the second signal may obtain the second signal by subtracting the sixth signal from the fifth signal.

In one embodiment, the first region of the skin may be a subcutaneous blood vessel, and the second region of the skin may be the skin excluding the subcutaneous blood vessel.

In one embodiment, the skin environment signals may include signals for one or more of the changes in the blood flow rate, the thickness of the blood vessels, and the skin color.

The present invention provides an apparatus for correction of non-invasive blood glucose measurement. The apparatus may include a means for irradiating white light on the skin by using a white light source, a means for filtering the white light reflected from the skin by a first wavelength filter and a second wavelength filter, a means for obtaining a first signal including a blood glucose signal and a pulse signal based on a video image generated by the white light filtered by the first wavelength filter, a means for obtaining a second signal including a pulse signal based on a video image generated by the white light filtered by the second wavelength filter, a means for obtaining a blood glucose signal by subtracting the second signal from the first signal, and a means for calculating the amount of blood glucose in a subcutaneous blood vessel based on the obtained blood glucose signal.

In one embodiment, a video image generated by the reflected white light filtered by a first wavelength filter includes a third signal which includes a blood glucose signal, a pulse signal, and a skin environment signal from the first region of the skin, and a fourth signal that includes a skin environment signal from the second region of the skin, and the means for obtaining the first signal may obtain the first signal by subtracting the fourth signal from the third signal.

In one embodiment, a video image generated by the reflected white light filtered by a second wavelength filter includes a fifth signal which includes a pulse signal and a skin environment signal from the first region of the skin, and a sixth signal that includes a skin environment signal from the second region of the skin, and the means for obtaining the second signal may obtain the second signal by subtracting the sixth signal from the fifth signal.

In one embodiment, the first region of the skin may be a subcutaneous blood vessel, and the second region of the skin may be the skin excluding the subcutaneous blood vessel.

In one embodiment, the skin environment signals may include signals for one or more of the changes in the blood flow rate, the thickness of the blood vessels, and the skin color.

According to the present invention, in addition to the blood glucose signal to be measured, a pulse signal that is measured together with the blood glucose signal can be corrected. Thus, an exact blood glucose signal excluding a pulse signal can be obtained. As the video image of the skin wherein the white light reflected from the skin has been filtered is used, the amount of blood glucose can be measured without collecting blood. Also, even if the amount of blood glucose is measured several times, the burden of the patient for blood collecting can be reduced. In addition, hygienic problems or the risk of infection that may occur during the process of blood collecting can be avoided.

Further, fundamental blood glucose signals can be extracted in real time. Accordingly, there is an advantage that the changes in the amount of blood glucose over time can be checked.

According to the present invention, there is an advantage that, by correcting noise with respect to skin environment signals, fundamental blood glucose signals can be extracted regardless of the skin environment signals that individuals have.

In addition, an apparatus for correction of non-invasive blood glucose measurement according to the present invention extracts blood glucose signals by analyzing video images through an image sensor of a camera. Thus, the apparatus can be implemented in such a way that it is compact and convenient to carry. Accordingly, the cost spent in the manufacturing process of the apparatus can be reduced.

Hereinafter, with reference to the attached drawings, the examples of the present invention are explained in detail so that a person having ordinary knowledge in the technical field to which the present invention pertains can easily carry out the invention. The present invention can be implemented in various different forms, and is not limited to the examples explained herein.

FIG. 1 is a simplified diagram of a system for correction of non-invasive blood glucose measurement according to one embodiment of the present invention.

Referring to FIG. 1, the system for correction of non-invasive blood glucose measurement according to one embodiment of the present invention comprises a server (100), a plurality of cameras (200) that obtain video images by filtering the white light reflected from the skin, a communication network (300) connecting the plurality of cameras (200) and the server (100), and although not shown, a light source (400) that irradiates white light.

Specifically, the method for non-invasive blood glucose measurement using an image sensor of a camera according to the present invention can use a method of measuring the absolute value of blood glucose by precisely analyzing in pixel units a video image including a subcutaneous blood vessel obtained in a plurality of pixels through the image sensors (212 and 222) of the cameras (200), thereby figuring out the location of the blood vessel, and calculating the blood flow rate of the blood vessel from the thickness of the blood vessel and the blood flow velocity. However, in this method, there have been problems that signals that are detected in places other than blood vessels may influence the exact measurement value of blood glucose, and as blood glucose signals are micro signals that are very precise, changes in the blood flow rate according to heart beats and skin environment signals according to skin environments of individuals may become noise that interferes with quantitative analysis.

To solve such problems, the server (100) for carrying out the method for correction of non-invasive blood glucose measurement according to one embodiment of the present invention is characterized as being able to obtain fundamental blood glucose signals in real time by correcting the pulse signal indicating the changes in the blood flow rate according to heart beats and the skin environment signal that can change according to the location of detection, and at the same time, providing an apparatus for blood glucose measurement which is small and convenient to carry. The operations of the server (100) will be explained later.

In addition, the plurality of cameras (200) may comprise a blood glucose information camera (210) and a pulse information camera (220), and the blood glucose information camera (210) comprises a first wavelength filter (211) and an image sensor (212), and the pulse information camera (220) includes a second wavelength filter (221) and an image sensor (222). For the convenience of explanation, although FIG. 1 illustrates a plurality of cameras (200), the system for correction of non-invasive blood glucose measurement according to the present invention does not necessarily have a plurality of cameras comprising a plurality of filters and a plurality of image sensors, but one camera may comprise a plurality of filters and a plurality of image sensors, one image sensor of one camera may detect the same region as different video images, or a plurality of cameras may comprise one filter and a plurality of image sensors.

Meanwhile, the white light reflected from the skin passes through the lens of the blood glucose information camera (210) and the lens of the pulse information camera (220), and the light that passed through the blood glucose information camera (210) passes through the first wavelength filter (211), and the light that passed through the pulse information camera (220) passes through the second wavelength filter (221). The image sensor (212) of the blood glucose information camera (210) realizes a video image consisting of a plurality of pixels from the light that passed through the first wavelength filter (211), and the image sensor (222) of the pulse information camera (220) realizes a video image consisting of a plurality of pixels from the light that passed through the second wavelength filter (221). The blood glucose information camera (210) and the pulse information camera (220) can extract different information with respect to the same region of the skin by using special optical filters, i.e., the first wavelength filter (211) and the second wavelength filter (221).

Meanwhile, the communication network (300) performs a role of connecting the plurality of cameras (200) and the server (100). That is, the communication network (300) refers to a communication network that provides a contact route so that the plurality of cameras (200) can transmit and receive video images after they contact the server (100).

Meanwhile, the light source (400) may preferably be a white light source that has the broadest scope of wavelength, but is not limited to a white light source. The light source (400) performs role of irradiating light on the skin, and the light source (400) that irradiates light and the cameras (200) that generate video images by receiving the reflected light operate independently from each other.

Figure 2:
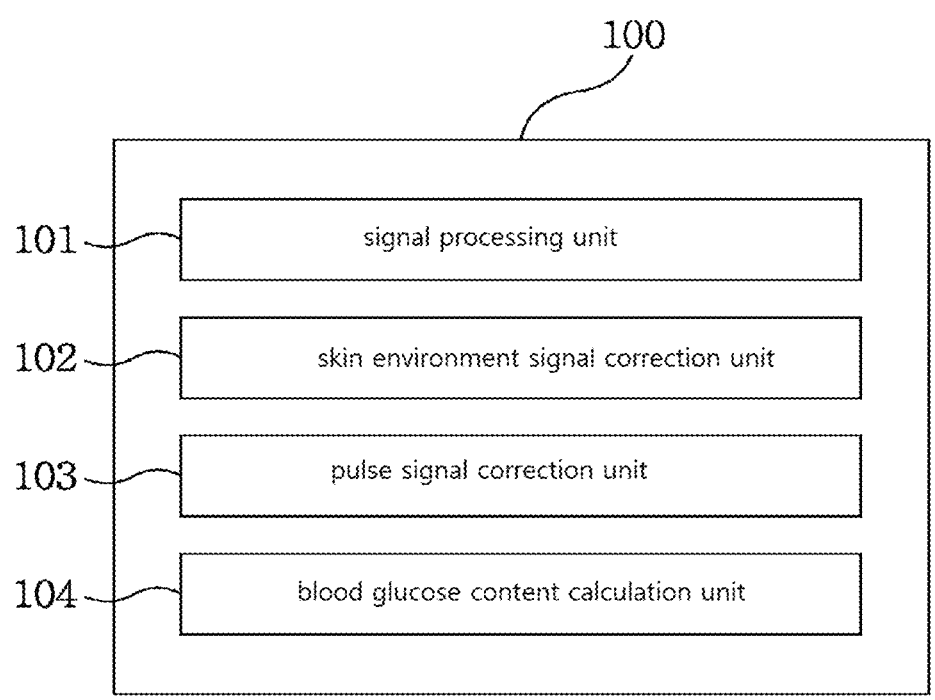
FIG. 2 is a block diagram illustrating the server of the system for correction of non-invasive blood glucose measurement according to the present invention.

FIG. 2 is a block diagram showing the server (100) of the system for correction of non-invasive blood glucose measurement.

Referring to FIG. 2, the server (100) of the system for correction of non-invasive blood glucose measurement according to one embodiment of the present invention comprises a signal processing unit (101) that generates a third signal to a sixth signal from the video images transmitted from the plurality of cameras (200), a skin environment signal correction unit (102) that subtracts a fourth signal and a sixth signal, which are skin environment signals, respectively from the generated third signal and the fifth signal, a pulse signal correction unit (103) that subtracts the second signal from which the sixth signal which is a skin environment signal has been subtracted from the first signal from which the fourth signal which is a skin environment signal has been subtracted, and a blood glucose content calculation unit (104) that calculates the amount of blood glucose based on the blood glucose signal obtained by subtracting the second signal from the first signal.

Specifically, in the signal processing unit (101) of the server (100), when a video image that passed through the first wavelength filter (211) of the blood glucose information camera (210) is analyzed, the scope of wavelength that corresponds to the blood glucose information spectrum is filtered, and the image sensor can generate a third signal that includes a blood glucose signal, a pulse signal, and a skin environment signal from the pixel in the part of the blood vessel of the video image, and a fourth signal that includes a skin environment signal from the pixel of the skin excluding the blood vessel. When a video image that passed through the second wavelength filter (30) of the pulse information camera (220) is analyzed, the scope of wavelength that corresponds to the pulse information spectrum is filtered, and the image sensor can generate a fifth signal that includes a pulse signal and a skin environment signal from the pixel in the part of the blood vessel of the video image, and a sixth signal that includes a skin environment signal from the pixel of the skin excluding the blood vessel. Here, the part of the blood vessel of the skin can be referred to as the first region, and the part of the skin excluding the blood vessel of the skin can be referred to as the second region.

The skin environment signal correction unit (102) of the server (100) subtracts the fourth signal that includes a skin environment signal from the skin excluding the blood vessel from the third signal that includes a blood glucose signal, a pulse signal, and a skin environment signal from the blood vessel, thereby obtaining the first signal where the environment signal has been corrected. The skin environment signal correction unit (102) of the server (100) also subtracts the sixth signal that includes a skin environment signal from the skin excluding the blood vessel from the fifth signal that includes a pulse signal and a skin environment signal from the blood vessel, thereby obtaining the second signal where the skin environment signal has been corrected.

The pulse signal correction unit (103) of the server (100) can subtract the second signal that includes a pulse signal from the first signal that includes a blood glucose signal and a pulse signal. The blood glucose signal where the pulse signal and the skin environment signal are corrected can be obtained by subtracting the second signal from the first signal. Accordingly, by correcting the pulse signal and the skin environment signal from the video image of the camera, an exact blood glucose signal can be extracted regardless of the changes in the blood flow rate according to heart beats and the skin environments of individuals.

The blood glucose content calculation unit (104) of the server (100) performs a role of calculating the blood flow rate by multiplying the thickness of the blood vessel and the blood flow velocity based on the blood glucose signal obtained by the pulse signal correction unit (103), and calculating the exact value of blood glucose based on the calculated blood flow rate.

Figure 3:
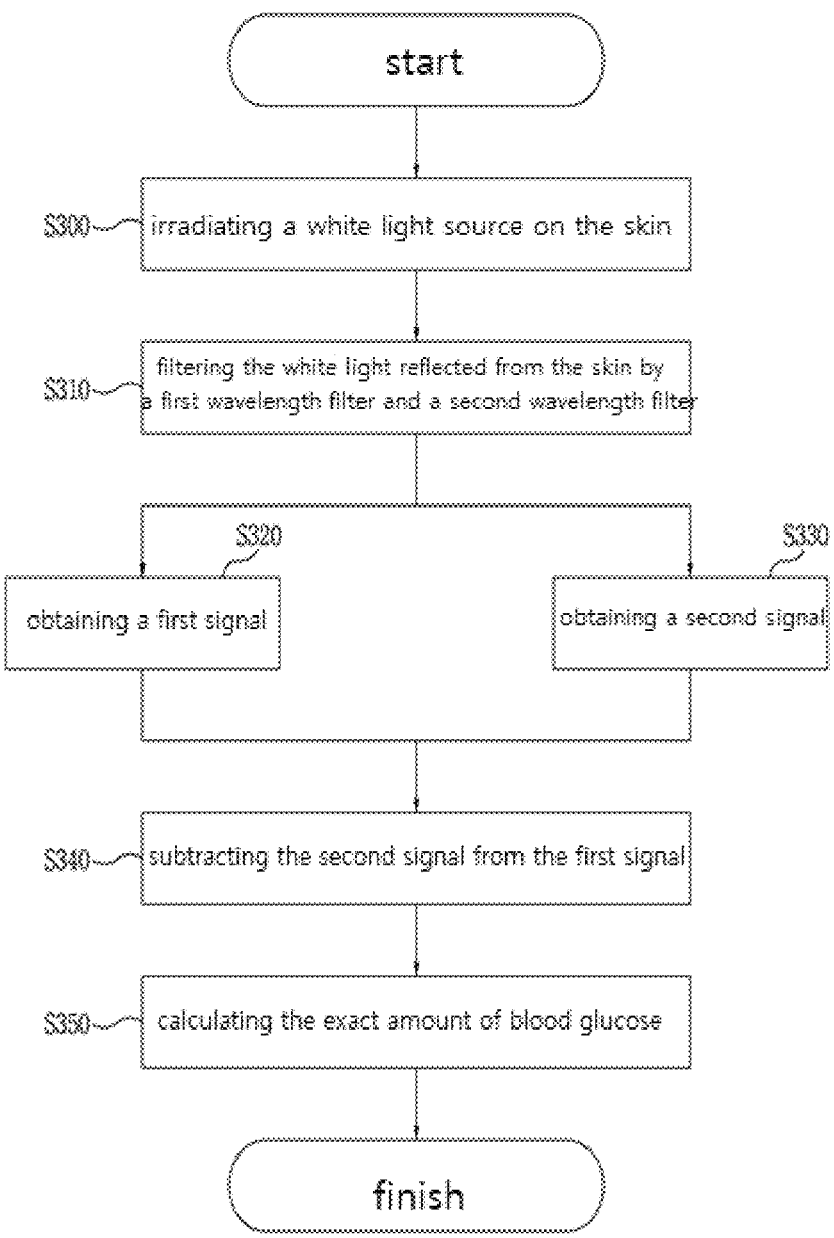
FIG. 3 illustrates a method for correction of non-invasive blood glucose measurement for obtaining a blood glucose signal wherein the pulse signal has been corrected according to the method of the present invention.

FIG. 3 is a flow chart that illustrates the method for non-invasive blood glucose measurement according to one embodiment of the present invention. The method for non-invasive blood glucose measurement according to one embodiment of the present invention is explained as follows with reference to the drawing.

First, white light is irradiated on the skin of the person to be measured by using the light source (400) (step S300). White light has the broadest scope of wavelength and is thus appropriate for blood glucose measurement. However, the light source is not limited to white light.

Figure 4:
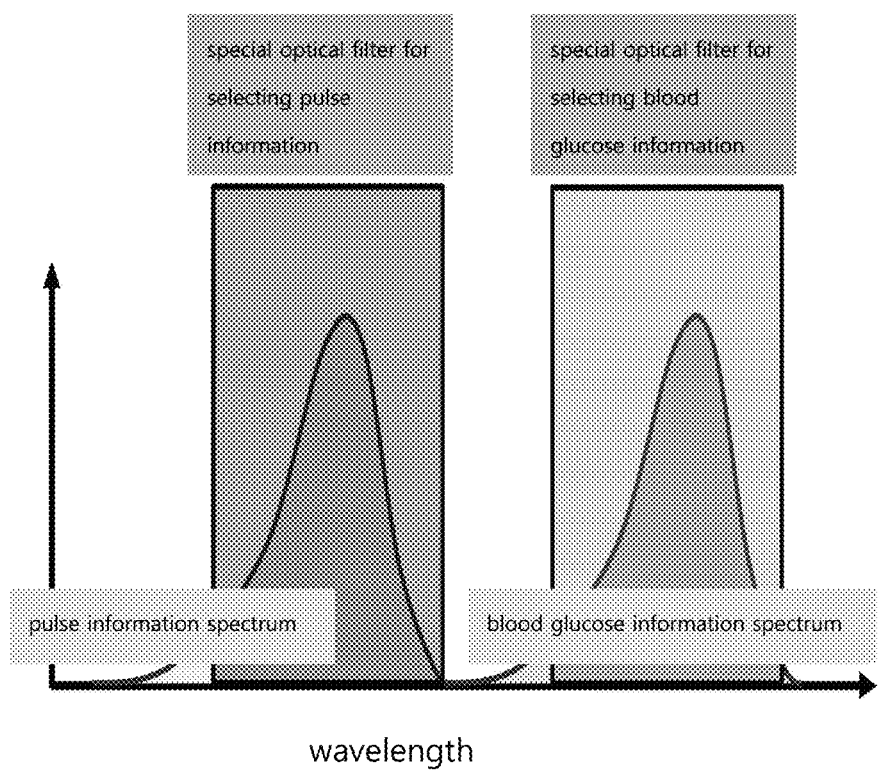
FIG. 4 illustrates the spectrum of a wavelength filtered by a first wavelength filter and a second wavelength filter.

The white light reflected from the skin on which the white light has been irradiated is filtered by passing through the first wavelength filter (211) and the second wavelength filter (221) of the cameras (200) (step S310). As illustrated in FIG. 4, when the light reflected from the skin is filtered by different special optical filters, different information on the spectrum can be obtained with respect to the same region of the skin depending on the scope of wavelength filtered by the special optical filters. Accordingly, the present invention filters the scope of wavelength corresponding to the pulse information spectrum by using the second wavelength filter (221) which is a special optical filter for selecting pulse information, and filters the scope of wavelength corresponding to the blood glucose information spectrum by using the first wavelength filter (211) which is a special optical filter for selecting blood glucose information. The light that passed through the first wavelength filter (211) of the blood glucose information camera (210) is realized as a video image consisting of a plurality of pixels through the image sensor (212) of the blood glucose information camera (210). The light that passed through the second wavelength filter (221) of the pulse information camera (220) is realized as a video image consisting of a plurality of pixels through the image sensor (222) of the pulse information camera (220). The server (100) receives the realized video images through the communication network (300).

Figure 5A:
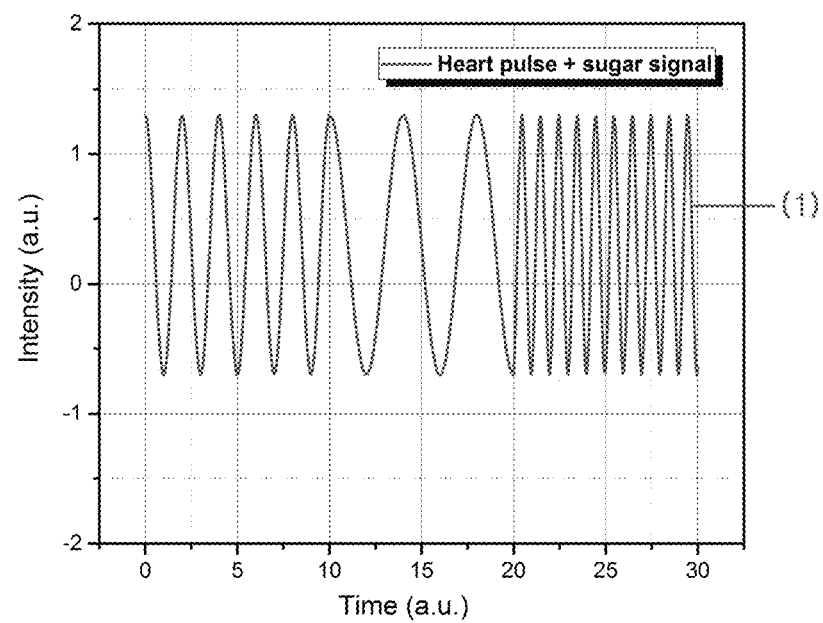
FIG. 5a illustrates a first signal including a blood glucose signal and a pulse signal.

The signal processing unit (101) of the server (100) can generate a third signal to a sixth signal, and the skin environment signal correction unit (102) can generate a first signal that includes a blood glucose signal and a pulse signal (step S320). Referring to FIG. 5a, it illustrates the first signal (1) that includes a blood glucose signal and a pulse signal obtained through the video image generated by the white light filtered by the first wavelength filter (211).

Figure 5B:
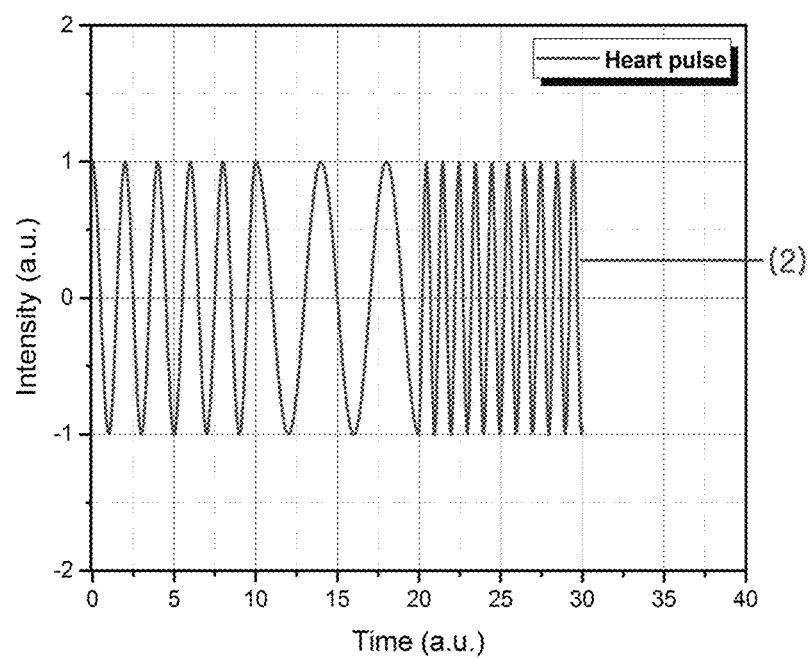
FIG. 5b illustrates a second signal including a pulse signal.

The signal processing unit (101) of the server (100) can generate a third signal to a sixth signal, and the skin environment signal correction unit (102) can generate a second signal including a pulse signal based on the fifth signal (step S330). Referring to FIG. 5b, it illustrates the second signal (2) including a pulse signal obtained through the video image generated by the white light filtered by the second wavelength filter (221).

Figure 5C:
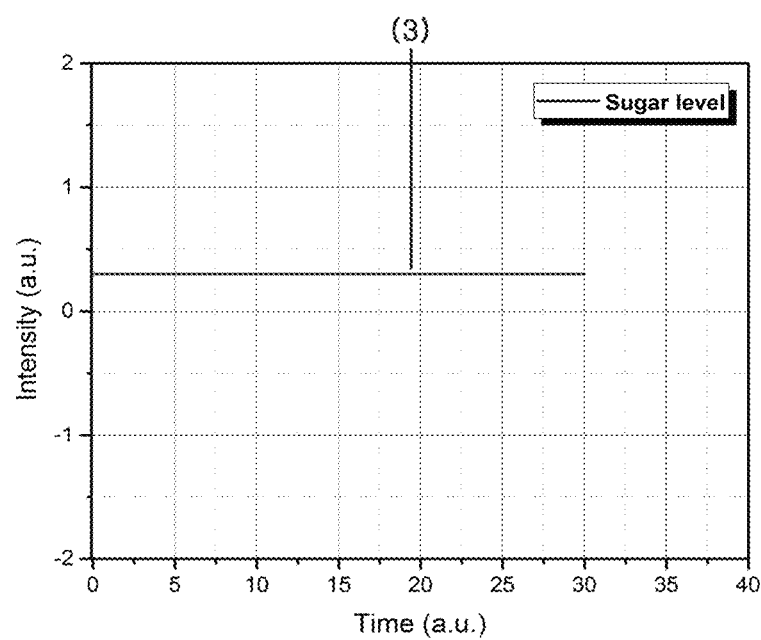
FIG. 5c illustrates a blood glucose signal obtained by subtracting the second signal from the first signal.

The pulse signal correction unit (103) of the server (100) subtracts the second signal from the obtained first signal (step S340). Referring to FIG. 5c, it illustrates a graph indicating the result of obtaining a blood glucose signal (3) by subtracting the second signal (2) wherein a pulse signal is measured from the first signal (1) wherein a blood glucose signal and a pulse signal are measured together. Here, it can be figured out that the blood glucose signal (3) is the corrected pulse signal, and the changes in the blood flow rate according to heart beats are not detected together.

The blood glucose content calculation unit (104) of the server (100) calculates the exact value of blood glucose based on the calculated blood flow rate and the obtained blood glucose signal (3) wherein the pulse signal has been corrected (step S350).

Figure 6:
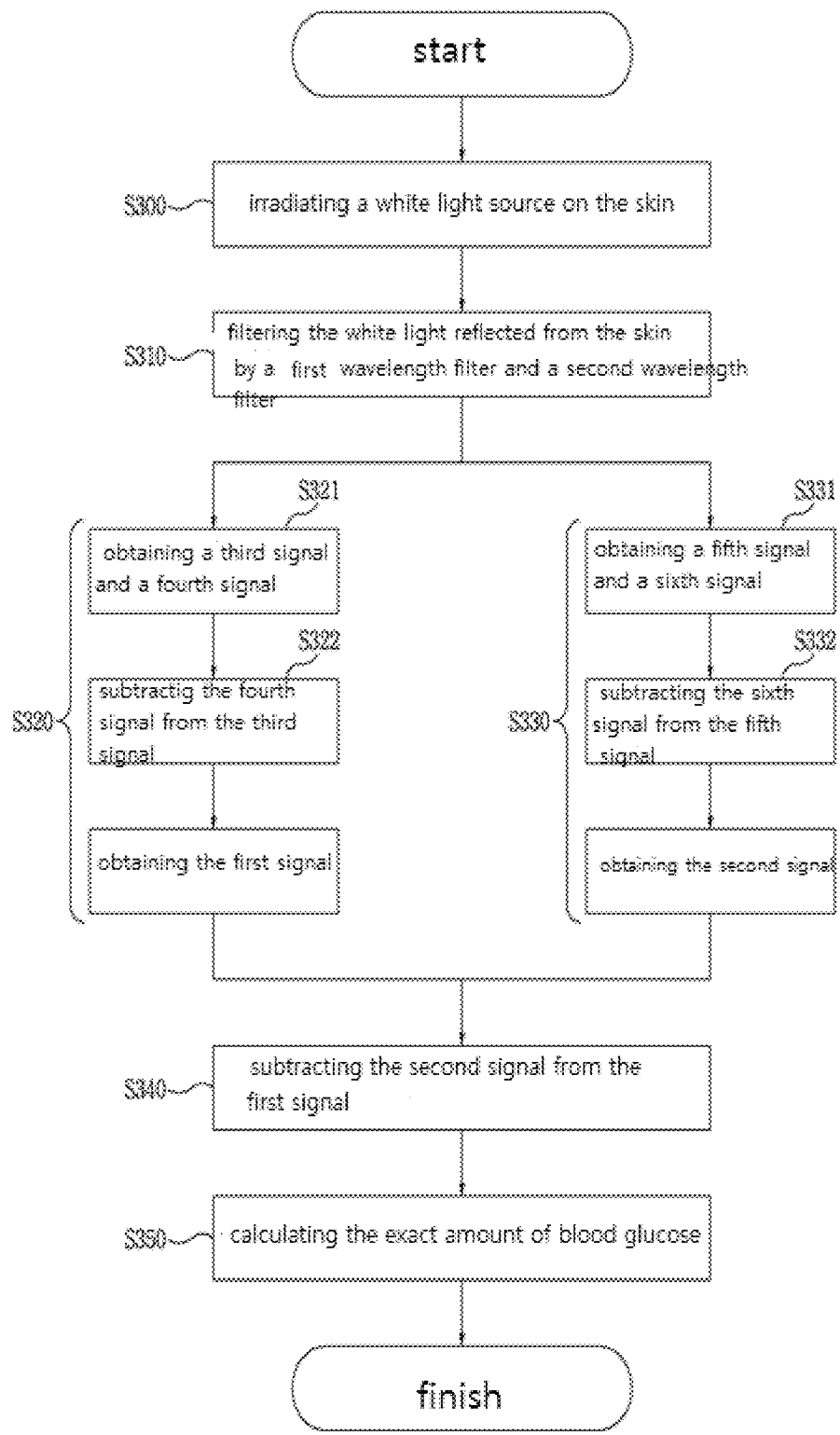
FIG. 6 illustrates a method for correction of non-invasive blood glucose measurement for obtaining a blood glucose signal wherein the pulse signal and the skin environment signal have been corrected according to the method of the present invention.

FIG. 6 is a flow chart illustrating a method for correction of non-invasive blood glucose measurement according to another example of the present invention. The steps explained above are not explained to avoid redundancy.

Figure 7:
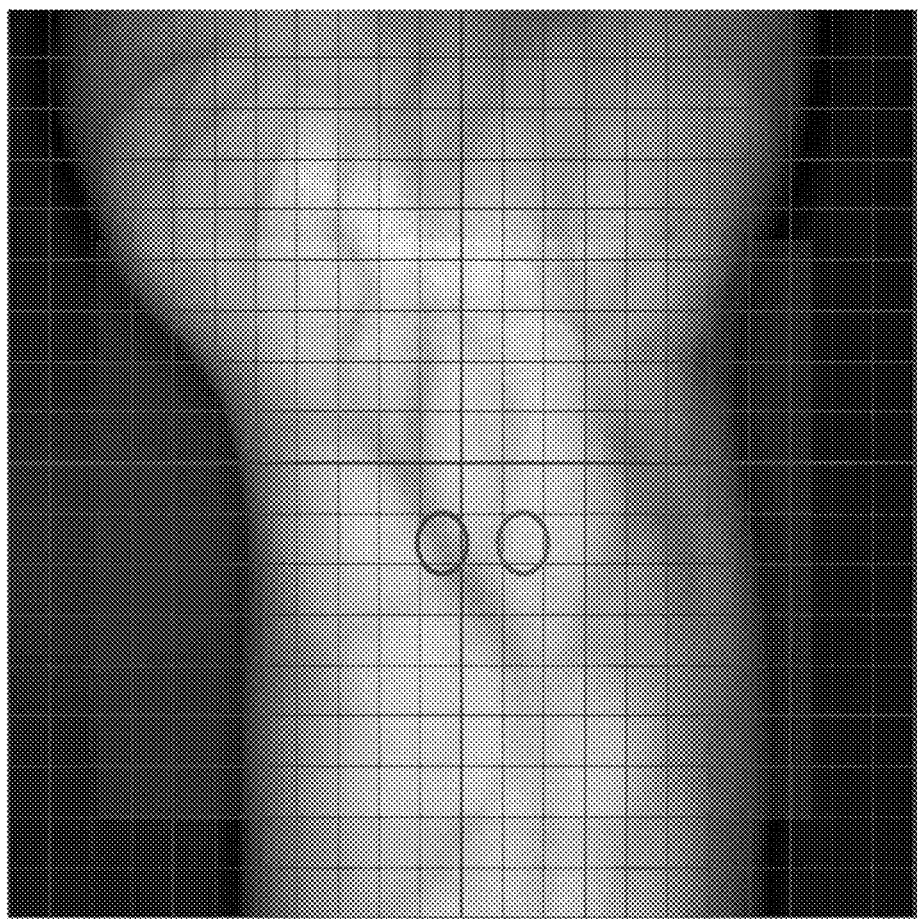
FIG. 7 illustrates a method for analyzing a video image obtained in a plurality of pixels by using an image sensor in pixels.
Figure 7:
Figure 7:
Figure 7:
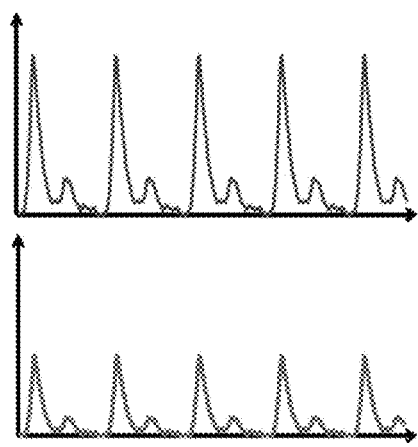

The step of obtaining the first signal (step S320) comprises the step of obtaining a third signal including a blood glucose signal, a pulse signal, and a skin environment signal, and a fourth signal including a skin environment signal in the signal processing unit (101) of the server (100) (step S321), and the step of subtracting the fourth signal from the third signal in the skin environment signal correction unit (102) (step S322). In this regard, FIG. 7 illustrates information obtained by the signal processing unit (101) of the server (100) by analyzing information received by each pixel of the image sensor in pixel units, and separating the pixels corresponding to the blood vessel and the pixels corresponding to the skin excluding the blood vessel. As can be seen from the graph in the lower part of FIG. 7, the signal obtained from the pixels where the blood vessel is located is different from the signal obtained from the pixels of the skin excluding the blood vessel. In particular, the signal obtained from the skin excluding the blood vessel can correspond to a skin environment signal. By subtracting the skin environment signal obtained in such a way from the signal obtained from the pixels where the blood vessel is located, the present invention can correct the errors according to the skin environments of individuals.

Going back to step S321, the signal processing unit (101) of the server (100) can obtain a third signal including a blood glucose signal, a pulse signal, and a skin environment signal from the pixels where the blood vessel is located, by analyzing the location of the blood vessel in pixel units from the video image consisting of a plurality of pixels that passed through the first wavelength filter (211). Also, the signal processing unit (101) of the server (100) can obtain a fourth signal that includes a skin environment signal from the pixels in the location of the skin excluding the blood vessel. The skin environment signal correction unit (102) of the server (100) can obtain a first signal wherein the skin environment signal has been corrected by subtracting the fourth signal from the third signal.

The step of obtaining the second signal (step S330) comprises the step of obtaining a fifth signal including a pulse signal and a skin environment signal, and a sixth signal including a skin environment signal in the signal processing unit (101) of the server (100) (step S331), and the step of obtaining the second signal by subtracting the sixth signal from the fifth signal in the skin environment signal correction unit (102) (step S332). More specifically, since the signal processing unit (101) of the server (100) can analyze the information received by each pixel of the image sensor per pixel, it can obtain information by separating the pixels corresponding to the blood vessel and the pixels corresponding to the skin excluding the blood vessel. Therefore, the signal processing unit (101) of the server (100) can obtain the fifth signal including a pulse signal and a skin environment signal from the pixels where the blood vessel is located, by analyzing the location of the blood vessel in pixel units from the video image consisting of a plurality of pixels that passed through the second wavelength filter (221). Also, the signal processing unit (101) of the server (100) can obtain the sixth signal including a skin environment signal from the pixels in the location of the skin excluding the blood vessel. The skin environment signal correction unit (102) of the server (100) can obtain the second signal wherein the skin environment signal has been corrected by subtracting the sixth signal from the fifth signal.

The pulse signal correction unit (103) of the server (100) can obtain a blood glucose signal wherein the skin environment signal and the pulse signal have been corrected (S350), by subtracting the second signal from the first signal wherein the skin environment signal has been corrected (S340).

The present invention is directed to extracting an exact blood glucose signal by irradiating white light on the skin of the person whose blood glucose is to be measured, filtering the light reflected from the skin by a filter having a specific wavelength, and subtracting several signals obtained by analyzing the filtered light with an image sensor. According to the present invention, in addition to the blood glucose signal to be measured, a pulse signal that is measured together with the blood glucose signal can be corrected. Thus, an exact blood glucose signal excluding a pulse signal can be obtained. As the video image of the skin wherein the white light reflected from the skin has been filtered is used, the amount of blood glucose can be measured without collecting blood. Also, even if the amount of blood glucose is measured several times, the burden of the patient about blood collecting can be reduced. In addition, hygienic problems or the risk of infection that may occur during the process of blood collecting can be avoided.

Further, fundamental blood glucose signals can be extracted in real time. Accordingly, there is an advantage that the changes in the amount of blood glucose over time can be checked.

According to the present invention, there is an advantage that, by correcting noise with respect to skin environment signals, fundamental blood glucose signals can be extracted regardless of the skin environment signals that individuals have.

In addition, an apparatus for correction of non-invasive blood glucose measurement according to the present invention extracts blood glucose signals by analyzing video images through an image sensor of a camera. Thus, the apparatus can be implemented in such a way that it is small and convenient to carry. Accordingly, the cost spent in the manufacturing process of the apparatus can be reduced.

With respect to the examples of the present invention that are disclosed in the main body, specific structural or functional explanations were suggested only with the purpose of explaining the examples of the present invention. Thus, the examples of the present invention can be carried out in various forms, and should not be interpreted to be limited to the examples explained in the main body. The statements regarding "one example," "one characteristic," "one embodiment" or "characteristics" in the overall descriptions of the present specification mean that the specific characteristic, structure, or characteristics explained with respect to such characteristics and/or examples are included in at least one characteristic and/or example in the gist claimed. Therefore, the expressions "in one example," "one embodiment," "in one characteristic," or "characteristics" appeared in several parts of the present specification do not necessarily refer to the same characteristics and/or examples. In addition, specific characteristics, structures, or characteristics can be combined with at least one example and/or characteristic.

Various modifications can be made to the present invention, and the present invention can have various forms. Thus, specific examples will be illustrated in the drawings, and will be explained in detail herein. However, the examples are not intended to limit the present invention to a specific form of embodiment. Instead, the examples should be understood to include all the modifications, equivalents or replacements included in the idea and the technical scope of the present invention.

Terms such as "a first" and "a second" can be used to explain various elements. However, the elements should not be limited by such terms. The terms can be used with the purpose of distinguishing an element from another element. For example, a first element can be referred to as a second element without deviating from the scope of protection of the present invention, and in a similar manner, a second element can also be referred to as a first element.

The terms used in the present invention are just used to explain specific examples, and are not intended to limit the present invention. A singular expression includes the plural expression, unless explicitly meant differently in terms of context. In the present invention, terms such as "include," "comprise" or "have" should be understood to mean that the explained characteristics, numbers, steps, operations, elements, components, or a combination thereof exist, and not to preclude the existence of one or more other characteristics, numbers, steps, operations, elements, components, or a combination thereof or the possibility of adding them.

Unless defined otherwise, all the terms used herein including technical or scientific terms have the same meaning as generally understood by a person having ordinary skill in the art to which the present invention pertains. Terms as defined in dictionaries that are generally used should be interpreted to have the same meaning as they have in the context of related technologies. Also, unless defined clearly in the present application, the terms should not be interpreted to have idealistic or excessively perfunctory meaning.

DESCRIPTION OF REFERENCE NUMERALS

100: server
200: a plurality of cameras
300: communication network
400: light source

The invention claimed is:

1. A method for correction of non-invasive blood glucose measurement, comprising:
 irradiating light on the region of the skin to be measured;
 obtaining a pixel video image of the region of the skin including a subcutaneous blood vessel in real time from the light reflected from the skin by using an image sensor of a camera, the camera including a first wavelength filter for selection of blood glucose information, wherein the first wavelength filter filters the scope of wavelength that comprises a blood glucose information spectrum, and including a second wavelength filter for selection of pulse information, wherein the second wavelength filter filters the scope of wavelength that corresponds to a pulse information spectrum, and wherein obtaining the pixel video image in real time comprises:
  obtaining a first pixel video image in real time by passing the reflected light through the first filter; and
  obtaining a second pixel video image in real time by passing the reflected light through the second filter;
 identifying pixels corresponding to the subcutaneous blood vessel from the pixel video images obtained in real time, and selecting a first pixel that corresponds to a specific location on the skin from the identified pixels, and obtaining a first signal that indicates the changes in the pixel information over time in the first pixel of the first pixel video image, and obtaining a second signal that indicates the changes in the pixel information over time in the first pixel of the second pixel video image, the obtained first signal including the blood glucose information and the pulse information of a specific region of the subcutaneous blood vessel, and the obtained second signal including the pulse information of the specific region of the subcutaneous blood vessel;

obtaining a blood glucose signal, wherein a pulse signal has been corrected, in real time, by removing the second signal from the first signal; and calculating blood flow rate by using a thickness of the blood vessel and blood flow velocity, and calculating the amount of blood glucose from the calculated blood flow rate and the blood glucose signal.

2. The method for correction of non-invasive blood glucose measurement according to claim 1, wherein:
the pixel video image includes skin environment information, and
obtaining the first signal and the second signal comprises correcting the skin environment information.

3. The method for correction of non-invasive blood glucose measurement according to claim 2, wherein:
correcting the skin environment information comprises:
selecting a second pixel, from the pixel video image obtained in real time, that corresponds to a specific location on the skin where a subcutaneous blood vessel does not pass;
obtaining a third signal that indicates the changes in the pixel information over time in the second pixel of the first pixel video image;
obtaining a fourth signal that indicates the changes in the pixel information over time in the second pixel of the second pixel video image;
obtaining the first signal wherein the skin environment information has been corrected by removing the third signal from the signal that indicates the changes in the pixel information over time in the first pixel of the first pixel video image; and
obtaining the second signal wherein the skin environment information has been corrected by removing the fourth signal from the signal that indicates the changes in the pixel information over time in the first pixel of the second pixel video image.

4. The method for correction of non-invasive blood glucose measurement according to claim 3, wherein:
the first pixel that corresponds to the region identified as the subcutaneous blood vessel and the second pixel that corresponds to the region of the skin identified as where the subcutaneous blood vessel does not pass are adjacent pixels.

5. The method for correction of non-invasive blood glucose measurement according to claim 2, wherein:
the skin environment information is information with respect to one or more of the changes in the blood flow rate, the thickness of the blood vessels, and the skin color.

6. The method for correction of non-invasive blood glucose measurement according to claim 1, wherein:
the light is white light.

7. The method for correction of non-invasive blood glucose measurement according to claim 1, wherein:
the region of the skin including the subcutaneous blood vessel is the wrist.

8. The method for correction of non-invasive blood glucose measurement according to claim 1, characterized in that:
the blood glucose signal can be measured with only one pulse, so that real time check-up of blood glucose can be possible.

9. An apparatus for correction of non-invasive blood glucose measurement, comprising:

a light source that irradiates light on the region of the skin to be measured; and a camera including an image sensor for obtaining a pixel video image of the region of the skin including a subcutaneous blood vessel in real time from the light reflected from the skin, the camera including a first wavelength filter for selection of blood glucose information, wherein the first wavelength filter filters the scope of wavelength that comprises a blood glucose information spectrum, and including a second wavelength filter for selection of pulse information, wherein the second wavelength filter filters the scope of wavelength that corresponds to a pulse information spectrum, and the pixel video image including a first pixel video image obtained in real time by passing the reflected light through the first filter and a second pixel video image obtained in real time by passing the reflected light through the second filter; and a server including a signal processor configured to:
identify pixels corresponding to the subcutaneous blood vessel from the pixel video images obtained in real time, select a first pixel that corresponds to a specific location on the skin from the identified pixels, obtain a first signal that indicates the changes in the pixel information over time in the first pixel of the first pixel video image, and obtain a second signal that indicates the changes in the pixel information over time in the first pixel of the second pixel video image, the obtained first signal including the blood glucose information and the pulse information of a specific region of the subcutaneous blood vessel and the obtained second signal including the pulse information of the specific region of the subcutaneous blood vessel;

obtain a blood glucose signal, wherein a pulse signal has been corrected, in real time, by removing the second signal from the first signal; and calculate blood flow rate by using the thickness of the blood vessel and blood flow velocity, and calculate the amount of blood glucose from the calculated blood flow rate and the blood glucose signal.

10. The apparatus for correction of non-invasive blood glucose measurement according to claim 9, wherein:
the pixel video image includes skin environment information, and
the signal processor is configured to obtain the first signal and the second signal by correcting the skin environment information.

11. The apparatus for correction of non-invasive blood glucose measurement according to claim 10, wherein:
the signal processor is configured to, in order to correct the skin environment information:
select a second pixel that corresponds to a specific location on the skin where a subcutaneous blood vessel does not pass from the pixel video image obtained in real time;
obtain a third signal that indicates the changes in the pixel information over time in the second pixel of the first pixel video image;
obtain a fourth signal that indicates the changes in the pixel information over time in the second pixel of the second pixel video image;
obtain the first signal wherein the skin environment information has been corrected by removing the third signal from the signal that indicates the changes in the pixel information over time in the first pixel of the first pixel video image; and obtain the second signal wherein the skin environment information has been corrected by removing the fourth signal from the signal that indicates the changes in the pixel information over time in the second pixel of the second pixel video image.

12. The apparatus for correction of non-invasive blood glucose measurement according to claim 9, wherein:
the server is connected to the apparatus through the communication network.

* * * * *